(12) United States Patent
Ito et al.

(10) Patent No.: US 11,253,439 B2
(45) Date of Patent: Feb. 22, 2022

(54) METHOD FOR PRODUCING COSMETIC COATING (71) Applicant: KAO CORPORATION, Tokyo (JP)

(72) Inventors: Motoaki Ito, Matsudo (JP); Nobuyuki Asami, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/604,726

(22) PCT Filed: Apr. 18, 2018

(86) PCT No.: PCT/JP2018/015977
§ 371 (c)(1),
(2) Date: Oct. 11, 2019

(87) PCT Pub. No.: WO2018/194083
PCT Pub. Date: Oct. 25, 2018

(65) Prior Publication Data
US 2020/0155424 A1 May 21, 2020

(30) Foreign Application Priority Data
Apr. 18, 2017 (JP) .............................. JP2017-082072

(51) Int. Cl.
A61K 8/02 (2006.01)
A45D 34/04 (2006.01)
(Continued)

(52) U.S. Cl.
CPC .............. A61K 8/027 (2013.01); A45D 34/04 (2013.01); A61K 8/34 (2013.01); A61K 8/8129 (2013.01);
(Continued)

(58) Field of Classification Search
None
See application file for complete search history.

(56) References Cited

U.S. PATENT DOCUMENTS 4,161,557 A 7/1979 Suzuki et al.
5,665,368 A 9/1997 Lentini et al.
(Continued)

FOREIGN PATENT DOCUMENTS

CN 100358487 A 1/2008
CN 103025784 A 4/2013
(Continued)

OTHER PUBLICATIONS

International Search Report dated Jun. 19, 2018 in PCT/JP2018/015977 filed Apr. 18, 2018.
(Continued)

Primary Examiner — Kyung S Chang
(74) Attorney, Agent, or Firm — Oblon, McClelland, Maier & Neustadt, L.L.P.

(57) ABSTRACT

Methods for producing a cosmetic coating on a skin surface, by: (A) electrostatically spraying a composition comprising component (a) one or more volatile substances selected from the group consisting of water, an alcohol and a ketone, and component (b) a polymer having a film-forming ability directly onto the skin to form a coating on the skin surface; and
(B) subsequently applying a powder-containing cosmetic on the formed coating, afford cosmetic coatings which can be removed without using a cleansing agent.

24 Claims, 1 Drawing Sheet (51) Int. Cl.
*A61K 8/34* (2006.01)
*A61K 8/81* (2006.01)
*A61K 8/87* (2006.01)
*A61Q 1/02* (2006.01)
*A61Q 17/04* (2006.01)

(52) U.S. Cl.
CPC ............... *A61K 8/87* (2013.01); *A61Q 1/02* (2013.01); *A61Q 17/04* (2013.01)

(56) References Cited

U.S. PATENT DOCUMENTS

| | | |
|---|---|---|
| 6,298,864 B1 | 10/2001 | Gueret |
| 6,514,504 B1 | 2/2003 | Yen et al. |
| 6,531,142 B1 | 3/2003 | Rabe et al. |
| 2002/0192252 A1 | 12/2002 | Ying Yen et al. |
| 2003/0228339 A1 | 12/2003 | El-Nokaly et al. |
| 2004/0021017 A1 | 2/2004 | Sumiyoshi et al. |
| 2005/0287103 A1 | 12/2005 | Filippi et al. |
| 2013/0058880 A1 | 3/2013 | Dong |
| 2013/0142852 A1 | 6/2013 | Tojo et al. |
| 2014/0328776 A1 | 11/2014 | Dong |
| 2015/0335569 A1 | 11/2015 | Ao et al. |
| 2015/0342855 A1 | 12/2015 | Ao et al. |

FOREIGN PATENT DOCUMENTS

| | | |
|---|---|---|
| EP | 0 933 039 A1 | 8/1999 |
| EP | 1 478 470 | 11/2004 |
| JP | 2003-506470 A | 2/2003 |
| JP | 2003-507165 A | 2/2003 |
| JP | 2005-527548 A | 9/2005 |
| JP | 2005-350466 A | 12/2005 |
| JP | 2006-104211 A | 4/2006 |
| JP | 2012-12317 A | 1/2012 |
| JP | 2016-503037 A | 2/2016 |
| JP | 2018-177724 A | 11/2018 |
| WO | WO 01/12137 A1 | 2/2001 |
| WO | WO 01/12139 A1 | 2/2001 |
| WO | WO 01/12335 A1 | 2/2001 |
| WO | WO 03/072263 A1 | 9/2003 |
| WO | WO 2011/064719 A1 | 6/2011 |

OTHER PUBLICATIONS

Extended European Search Report dated Dec. 7, 2020 in corresponding European Patent Application No. 18788218.8, 10 pages.

METHOD FOR PRODUCING COSMETIC COATING

FIELD OF THE INVENTION

The present invention relates to a method for producing a cosmetic coating on the skin.

BACKGROUND OF THE INVENTION

Many cosmetics, such as powder-containing foundations, contain oily components and powders, and various contrivances are usually made in order to improve the cosmetic quality. As one of them, a method for forming a coating by electrostatic spraying is known. For example, Patent Literature 1 discloses a method for treating skin comprising electrostatically spraying a composition onto the skin. The composition used in the method contains a liquid-insulating material, a conductive material, a particulate powder material, and a thickener. Typically, a cosmetic product or skin-care composition containing a pigment is used as the composition. Specifically, a cosmetic foundation is used as the composition. That is, the inventions disclosed in Patent Literature 1 are primarily envisioned for cosmetic purposes by electrostatically spraying a cosmetic foundation to cosmetically decorate the skin.

Patent Literature 2 discloses disposable cartridges for use in electrostatic spraying devices for cosmetics. The electrostatic spraying device is of a hand-held and self-contained type. This electrostatic spraying device is used for spraying cosmetic foundations in the same manner as the Patent Literature 1 above.

(Patent Literature 1) JP-A-2006-104211
(Patent Literature 2) JP-A-2003-507165

The present invention relates to a method for producing a cosmetic coating on a skin surface, the method comprising Step A) of electrostatically spraying a composition comprising component (a) one or more volatile substances selected from the group consisting of water, an alcohol and a ketone and component (b) a polymer having a film forming ability directly onto the skin to form a coating on the skin surface; and Step B) of subsequently applying a powder-containing cosmetic on the formed coating.

DETAILED DESCRIPTION OF THE INVENTION

However, when removing makeup cosmetics, it is common to use cleansing agents for rinsing or wiping with water. Therefore, there is an issue that it is necessary to move to a place where there is a washstand, a bathroom, or a mirror stand. Cosmetic coatings formed by the methods described in Patent Literatures 1 and 2 likewise require the use of cleansing agents or the like in order to remove cosmetics such as foundations.

Accordingly, the present invention provides a method for forming a cosmetic coating which allows the cosmetic to be removed without the use of cleansing agents or the like.

Therefore, as a result of extensive studies, the present inventors have found that, if a composition containing a particular component is electrostatically sprayed onto the skin to form a coating on the skin surface and then a powder-containing cosmetic is applied onto the coating surface, not only a cosmetic coating having less kindness and good cosmetic durability is obtained, but also a cosmetic can be easily removed simply by peeling with fingers without using a cleansing agent, as compared with the case of a powdered cosmetic alone, and the present invention is completed.

The cosmetic coating obtained by the method of the present invention is excellent in cosmetic durability because the coating formed by electrostatic spraying masks the skin surface and therefore the cosmetic coating is less susceptible to makeup collapse as compared with a case of using the powder cosmetic alone. In addition, not only the adhesion of the powder directly to the skin is prevented, but also the cosmetic coating can be easily and successfully stripped off by merely peeling with a finger without using a cleansing agent, and the cosmetic can be removed from the skin.

The method for producing a cosmetic coating of the present invention comprises Step A) followed by Step B). That is, first, Step A is performed, of forming a coating on the skin surface by electrostatically spraying a composition comprising a component (a) and a component (b) (hereinafter, sometimes referred to as a spraying composition) directly onto the skin:

(a) one or more volatile substances selected from the group consisting of water, an alcohol and a ketone, and (b) a polymer having a film-forming ability.

The (a) volatile substance represents a substance having volatility in a liquid state. In the spraying composition, component (a) is discharged from the nozzle tip toward the skin after the spraying composition placed in the electric field is sufficiently charged, and when component (a) evaporates, the charge density of the spraying composition becomes excessive, and component (a) evaporates further while being further refined by Coulomb repulsion, and finally, component (a) is blended for the purpose of forming a dry coating on the skin. For this purpose, the volatile substance preferably has a vapor pressure at 20° C. of 0.01 kPa or more and 106.66 kPa or less, more preferably 0.13 kPa or more and 66.66 kPa or less, further more preferably 0.67 kPa or more and 40.00 kPa or less, and even more preferably 1.33 kPa or more and 40.00 kPa or less.

Among the (a) volatile substances, for example, monovalent chain aliphatic alcohols, monovalent cyclic aliphatic alcohols, and monovalent aromatic alcohols, are suitable for use as alcohols. Examples of the monovalent chain aliphatic alcohol include C1-C6 alcohol, the monovalent cyclic aliphatic alcohol includes C4-C6 cyclic alcohol, and the monovalent aromatic alcohol includes benzyl alcohol, and phenylethyl alcohol. Specific examples thereof include ethanol, isopropyl alcohol, butyl alcohol, phenylethyl alcohol, n-propanol, and n-pentanol. One or more of these alcohols can be used.

Among the (a) volatile substance, examples of the ketone include a C1-C4 dialkyl ketone, for example, acetone, methyl ethyl ketone, methyl isobutyl ketone. These ketones can be used alone or in combination of two or more.

The (a) volatile substance is more preferably one or more selected from the group consisting of ethanol, isopropyl alcohol, butyl alcohol and water, more preferably one or more selected from the group consisting of ethanol and butyl alcohol, and even more preferably a volatile substance at least containing ethanol.

The content of component (a) in the spraying composition is preferably 30 mass % or more, more preferably 55 mass % or more, and even more preferably 60 mass % or more. It is also preferably 98 mass % or less, more preferable 96 mass % or less, and even more preferably 94 mass % or less. The content of component (a) in the spraying composition is preferably 30 mass % or more and 98 mass % or less, more preferably 55 mass % or more and 96 mass % or less, and even more preferably 60 mass % or more and 94 mass % or less. By containing component (a) in the spraying composition at this ratio, the spraying composition can be sufficiently volatilized when the electrostatic spraying method is performed.

The content of ethanol is preferably 50 mass % or more, more preferably 65 mass % or more, and even more preferably 80 mass % or more, based on the total amount of the (a) volatile substance. It is preferable that the content be 100 mass % or less. The content of ethanol is preferably 50 mass % or more and 100 mass % or less, more preferably 65 mass % or more and 100 mass % or less, and even more preferably 80 mass % or more and 100 mass % or less, based on the total amount of the (a) volatile substance.

The (b) polymer having a film-forming ability represents generally a substance which can be dissolved in the (a) volatile substance. Here, dissolving means a dispersed state at 20° C., and the dispersed state means a visually uniform state, preferably a visually transparent or translucent state.

As the polymer having a film-forming ability, a polymer suitable for the nature of the volatile substance of the (a) volatile component may be used. Specifically, a polymer having a film-forming ability is roughly classified into a water-soluble polymer and a water-insoluble polymer. As used herein, the term "water-soluble polymer" means a polymer having a property in which, after weighing the polymer 1 g under the atmosphere of 1 atm and at 23° C., the polymer is immersed in 10 g of ion-exchanged water, and 0.5 g or more of the immersed polymer is dissolved in water after a lapse of 24 hours. The "water insoluble polymer" in the present specification refers to a polymer having a property that 0.5 g or more of the polymer immersed in 10 g of ion-exchanged water is not dissolved after 24 hours after weighing the polymer 1 g under the atmosphere of 1 atm and 23° C.

Examples of the water-soluble polymer having a film-forming ability include a mucopolysaccharide such as pullulan, hyaluronic acid, chondroitin sulfate, poly-γ-glutamic acid, modified corn starch, β-glucan, a gluco-oligosaccharide, heparin, and keratosulfuric acid; a natural polymer such as cellulose, pectin, xylan, lignin, glucomannan, galacturonic acid, thyrium seed gum, tamarind seed gum, gum arabic, a soy water-soluble polysaccharide, alginic acid, carrageenan, laminan, agar (agarose), fucoidan, methylcellulose, hydroxypropyl cellulose, and a low molecular weight polyvinyl alcohol; a synthetic polymer such as a partially saponified polyvinyul alcohol (not used in combination with a crosslinking agent), a low saponified polyvinyl alcohol, polyvinyl pyrrolidone (PVP), polyethylene oxide, and sodium polyacrylate. These water-soluble polymers can be used alone or in combination of two or more. Among these water-soluble polymers, pullulan, and a synthetic polymer such as a partially saponified polyvinyl alcohol, a low saponified polyvinyl alcohol, polyvinyl pyrrolidone, and polyethylene oxide are preferably used from the viewpoint of easiness in production of the coating. When polyethylene oxide is used as the water-soluble polymer, its number average molecular weight is preferably 50,000 or more and 3,000,000 or less, more preferably 100,000 or more and 2,500,000 or less.

Meanwhile, examples of the water-insoluble polymer having a film-forming ability include, a fully saponified polyvinyl alcohol which can be insolubilized after the formation of a coating, a partially saponified polyvinyl alcohol which can be cross linked after the formation of a coating by using in combination with a crosslinking agent, an oxazoline-modified silicone such as a poly(N-propanoylethyleneimine)-dimethylsiloxane/γ-aminopropylmethylsiloxane copolymer, polyvinyl acetal diethyleminoacetate, Zein (a main component of corn protein), polyester, polylactic acid (PLA), an acrylic resin (e.g., a polyacrylonitrile resin, a polymethacrylic acid resin), a polystyrene resin, a polyvinyl butyral resin, a polyethylene terephthalate resin, a polybutylene terephthalate resin, a polyurethane resin, a polyamide resin, a polyimide resin, a polyamide-imide resin. These water insoluble polymers can be used alone or in combination of two or more. Among these water-insoluble polymers, it is preferable to use one or more selected from the group consisting of a fully saponified polyvinyl alcohol which can be insolubilized after the formation of a coating, a partially saponified polyvinyl alcohol which can be crosslinked after the formation of a coating by using in combination with a crosslinking agent, a polyvinyl butyral resin, a polyurethane resin, an oxazoline-modified silicone such as a poly(N-propanoylethyleneimine) graft-dimethylsiloxane/γ-aminopropylmethylsiloxane copolymer, polyvinyl acetal diethylaminoacetate and Zein, and it is more preferable to use one or more selected from the group consisting of a polybutyral resin and a polyurethane resin.

The content of component (b) in the spraying composition is preferably 2 mass % or more, more preferably 4 mass % or more, and even more preferably 6 mass % or more. It is also preferably 50 mass % or less, more preferably 45 mass % or less, and even more preferably 40 mass % or less. The content of component (b) in the spraying composition is preferably 2 mass % or more and 50 mass % or less, more preferably 4 mass % or more and 45 mass % or less, and even more preferably 6 mass % or more and 40 mass % or less. Incorporation of component (b) in the spraying composition at this ratio enables to successfully form a coating composed of a fiber deposit, which masks the surface of the raw skin, and is resistant to makeup collapse and has excellent cosmetic durability even after a lapse of time.

The content ratio of component (a) to component (b) in the spraying composition, ((a)/(b)), is preferably 0.5 or more and 40 or less, more preferably 1 or more and 30 or less, and more preferably 2 or more and 25 or less, from the viewpoint that component (a) can be sufficiently volatilized when the electrostatic spraying method is performed.

The content ratio of the (a) ethanol and component (b) in the spraying composition, ((a)/(b)), is preferably 0.5 or more and 40 or less, more preferably 1 or more and 30 or less, and even more preferably 2 or more and 25 or less, from the viewpoint that component (a) can be sufficiently volatilized when the electrostatic spraying method is performed.

The spraying composition may contain glycol. Examples of the glycol include ethylene glycol, propylene glycol, butylene glycol, diethylene glycol, dipropylene glycol, polypropylene glycol, and the like. From the viewpoint that component (a) can be sufficiently volatilized when the electrostatic spraying method is performed, the content of glycol is preferably 10 mass % or less, more preferably 3 mass % or less, preferably 1 mass % or less, and the spraying composition is preferably substantially free of glycol.

The spraying composition may contain a powder. Examples of the powder include a coloring pigment and a constitutive pigment, a pearl pigment, and an organic powder. From the viewpoint of imparting a smooth feel to the skin surface, the content of the powder in the composition is preferably 5 mass % or less, more preferably 3 mass % or less, further more preferably 1 mass % or less, and the spraying composition is preferafoly substantially free of powder.

The spraying composition may contain only components (a) and (b) described above, or may contain other component(s) in addition to components (a) and (b). Examples of the other components include an oil agent such as dilauroyl glutamate (phytosteryl/octyldodecyl), a surfactant, a UV protective agent, a perfume, a repellent, an antioxidant, a stabilizer, a preservative, an antiperspirant, and various vitamins. Each of these agents is not limited to the use as each agent, and other uses, for example, an antiperspirant can be used as a perfume depending on the purpose. Alternatively, it can be used for multiple purposes, for example, as an antiperspirant and as a perfume. When the spraying composition contains other component(s), the content ratio of the other component(s) is preferably 0.1 mass % or more and 30 mass % or less, and more preferably 0.5 mass % or more and 20 mass % or less.

In the method of the present invention, the spraying composition is electrostatically sprayed directly onto the skin to form a coating on the skin prior to application of the powder-containing cosmetic to the skin.

In performing the electrostatic spraying method, as the spraying composition, a composition having a viscosity at 25° C. of preferably 1 mPa·s or more, more preferably 10 mPa·s or more, and even more preferably 50 mPa·s or more is used. In addition, a material having a viscosity of 5,000 mPa·s or less, more preferably 2,000 mPa·s or less, and even more preferably 1,500 mPa·s or less at 25° C. is used. The viscosity of the spraying composition at 25° C. is preferably 1 mPa·s or more and 5,000 mPa·s or less, more preferably 10 mPa·s or more and 2,000 mPa·s or less, and more preferably 50 mPa·s or more and 1,500 mPa·s or less. By using a spraying composition having a viscosity in this range, it is possible to successfully form a coating, in particular a porous coating consisting of a fiber deposit, by means of an electrostatic spraying method. The formation of the porous coating is advantageous from the viewpoint of improving the prevention of skin evaporation, improving the adhesivity of the coating to the skin, and allowing peeling easily and completely when the coating is peeled from the skin. The viscosity of the spraying composition is measured at 25° C. by using a type E viscometer. As the E-type viscometer, for example, an E-type viscometer manufactured by Tokyo Meters Corporation can be used. In this case, the rotor No. 43 can be used as the rotor.

Figure 1:
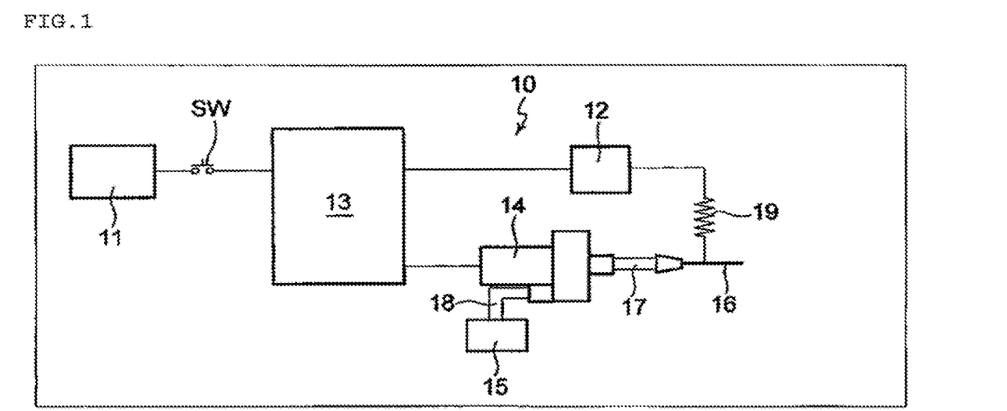
FIG. 1 is a schematic diagram showing a configuration of an electrostatic spraying device suitable for use in the present invention.

The spraying composition is sprayed directly onto the human skin by electrostatic spraying. Electrostatic spraying involves electrostatically spraying the spraying composition onto the skin using an electrostatic spraying device to form a coating by way of an electrostatic spraying. The electrostatic spraying device comprises a container containing a spraying composition, a nozzle for discharging the spraying composition, a supply device for supplying the spraying composition contained in the container to the nozzle, and a power supply for applying a voltage to the nozzle. FIG. 1 is a schematic diagram showing a configuration of an electrostatic spraying device preferably used in the present invention. The electrostatic spraying device 10 shown in FIG. 1 includes a low-voltage power supply 11. The low-voltage power supply 11 can generate a voltage of several volts or more and below 20 volts. For the purpose of enhancing the portability of the electrostatic spraying device 10, the low-voltage power supply 11 preferably comprises one or more batteries. Further, by using a battery as the low-voltage power supply 11, there is an advantage that replacement can be easily performed as necessary. Instead of the battery, an AC adapter or the like can be used as the low-voltage power supply 11.

The electrostatic spraying device 10 also includes a high-voltage power supply 12 is connected to the low-voltage power supply 11, and includes an electronic circuit (not shown) for boosting a voltage generated by the low-voltage power supply 11 to a high voltage. The booster circuit is generally composed of a transformer, a capacitor, a semiconductor element, and the like.

The electrostatic spraying device 10 further comprises an auxiliary electrical circuit 13. The auxiliary electric circuit 13 is interposed between the low-voltage power supply 11 and the high-voltage power supply 12, and has a function of adjusting the voltage of the low-voltage power supply 11 to stably operate the high-voltage power supply 12. Further, the auxiliary electric circuit 13 has a function of controlling the number of revolutions of a motor provided in a microgear pump 14, which will be described later. By controlling the rotation speed of the motor, the supply amount of the spraying composition from the container 15 of the spraying composition described later to the microgear pump 14 is controlled. A switch SW is mounted between the auxiliary electric circuit 13 and the low-voltage power supply 11 such that the electrostatic spraying device 10 can be turned on and off by turning the switch SW on and off.

The electrostatic spraying device 10 further comprises a nozzle 16. The nozzle 16 is made of a conductive material such as metal or a non-conductive material such as plastic, rubber, ceramic, and has a shape capable of discharging the spraying composition from the tip thereof. A microspace through which the spraying composition flows is formed in the nozzle 16 along the longitudinal direction of the nozzle 16. The size of the cross section of the microspace is preferably 100 μm or more and 1,000 μm or less in terms of diameter. The nozzle 16 communicates with the microgear pump 14 via a pipe 17. The pipe 17 may be conductive or non-conductive. The nozzle 16 is electrically connected to the high-voltage power supply 12. This makes it possible to apply a high voltage to the nozzle 16. In this case, in order to prevent an excessive current from flowing when a human body directly touches the nozzle 16, the nozzle 16 and the high-voltage power supply 12 are electrically connected via a current limiting resistor 19.

The microgear pump 14 communicating with the nozzle 16 via a pipe 17 functions as a supply device for supplying the nozzle 16 with the spraying composition contained in the container 15. The microgear pump 14 is operated by receiving a power supply from the low-voltage power supply 11. The microgear pump 14 is configured to supply a predetermined amount of the spraying composition to the nozzle 16 under the control of the auxiliary electric circuit 13.

The container 15 is connected to the microgear pump 14 via a flexible pipe 18. Contained in the container 15 is the spraying composition. The container 15 preferably has a cartridge-type replaceable configuration.

Figure 2:
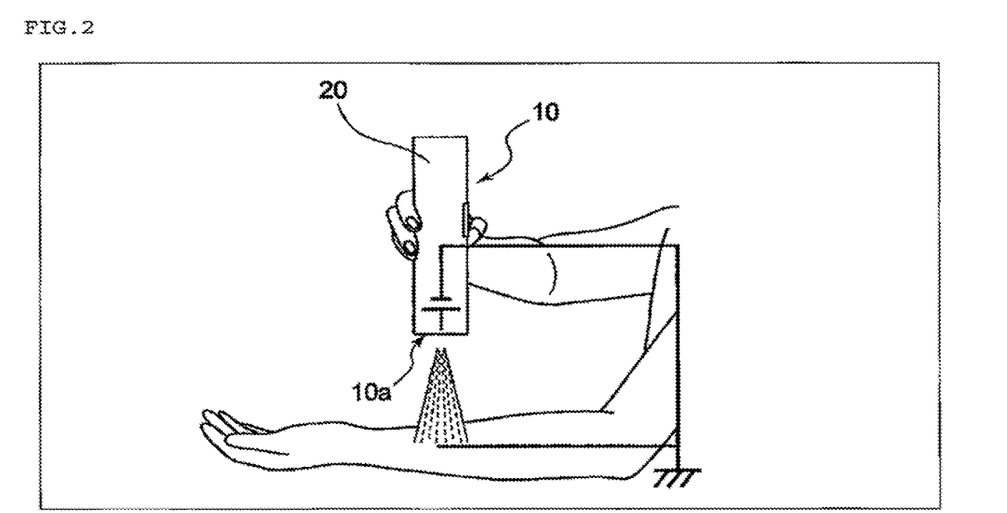
FIG. 2 is a schematic diagram showing a state in which an electrostatic spraying method is performed using an electrostatic spraying device.

The electrostatic spraying device 10 having the above configuration can be used, for example, as shown in FIG. 2. FIG. 2 shows an electrostatic spraying device 10 of the hand-held type having a size holdable by one hand. The electrostatic spraying device 10 shown in the same figure contains all of the members of the configuration diagram shown in FIG. 1 in the cylindrical housing 20. A nozzle, not shown, is disposed at one longitudinal end 10a of the housing 20. The nozzle is disposed in the housing 20 such that the blowing direction of the composition coincides with the longitudinal direction of the housing 20 and the nozzle is protruding toward the skin side, which is the coating formation object. By arranging the nozzle tip so as to protrude toward the coating formation object in the longitudinal direction of the housing 20, the spraying composition is hardly adhered to the housing, and the coating can be stably formed.

If the user intends to form a coating on the skin of the user's own, when the user operates the electrostatic spraying device 10, the user, i.e., the person who forms the coating on his/her own skin by electrostatic spraying, holds the device 10 by hand and directs one end 10a of the device 10, in which a nozzle, not shown, is located, to the site to be sprayed electrostatically. In FIG. 2, one end 10a of the electrostatic spraying device 10 is shown pointing inside the user's forearm. In this state, the device 10 is switched on to perform the electrostatic spraying method. When the device 10 is powered on, an electric field is generated between the nozzle and the skin. In the embodiment shown in FIG. 2, a positive high voltage is applied to the nozzle and the skin becomes the negative electrode. When an electric field is generated between the nozzle and the skin, the spraying composition at the tip of the nozzle is polarized by electrostatic induction, the tip portion thereof becomes conical, and droplets of the spraying composition charged from the tip of the cone are discharged into the air toward the skin along the electric field. When component (a) as a solvent evaporates from the spraying composition discharged into the space and charged, the charge density on the surface of the spraying composition becomes excessive, and spreads into the space by repeated refinement by Coulomb repulsion force, and reaches the skin. In this case, by appropriately adjusting the viscosity of the spraying composition, the sprayed composition can reach the skin in the form of droplets. Alternatively, while being discharged into the space, the volatile substance component (a) as a solvent may be volatilized from the composition to solidify a polymer having a film forming ability as a solute, and the fiber may be formed while being stretched and deformed by a potential difference, and the fiber may be deposited on the surface of the skin. For example, increasing the viscosity of a spraying composition tends to cause the composition to deposit on the surface of the skin in the form of fibers. As a result, a coating consisting of a fiber deposit is formed on the surface of the skin. Coatings of fiber deposits can also be formed by adjusting the distance between the nozzle and the skin and the voltage applied to the nozzle.

During the electrostatic spraying, a high potential difference is generated between the skin, which is the object to be coated, and the nozzle. However, because of very large impedance, the current extremely hardly flow through the human body. For example, the present inventors have confirmed that the current flowing through the human body during the electrostatic spraying step is several orders of magnitude smaller than the current flowing through the human body due to static electricity generated during normal living.

When a fiber deposit is formed by the electrostatic spraying method, the thickness of the fiber is preferably 10 nm or more, more preferably 50 nm or more, when expressed as a circle equivalent diameter. The thickness is preferably 3,000 nm or less, and more preferably 1,000 nm or less. The thickness of the fiber can be measured by observing the fiber at a magnification of 10,000× by, for example, scanning electron microscopy (SSM) observation, removing defects (clumps of fibers, crossing portions of fibers, and droplets) from the two-dimensional image, arbitrarily selecting 10 fibers, drawing a line orthogonal to the longitudinal direction of the fiber, and directly reading the fiber diameter.

The above-described fiber is a continuous fiber of infinite length in principle of production, but it is preferable have a length of at least 100 times or more of the thickness of the fiber. In the present specification, a fiber having a length of 100 times or more of the thickness of the fiber is defined as a "continuous fiber". The coating produced by the electrostatic spraying method is preferably a porous discontinuous coating composed of a deposit of continuous fibers. Such a form of coating not only can be handled as a single sheet as an aggregate, but also has the advantage that it has a very soft texture, and it is hard to be separated even when a shearing force is applied, and it is excellent in the followability to the body movement. In addition, there is an advantage that it is excellent in the dissipation of sweat generated from the skin. Further, the coating can be advantageously easily peeled off. In contrast, a continuous coating without pores is not easy to peel off and has a very low sweat dissipation property, so that the skin may be blistered.

Now that the spraying composition has turned fibrous, it reaches the skin in a charged state. Since the skin is also charged as described above, the fibers adhere to the skin by electrostatic forces. Since fine irregularities such as undulations are formed on the skin surface, the fibers more closely adhere to the surface of the skin together with the anchoring effect due to the irregularities. When the electrostatic spraying is completed in this manner, the power of the electrostatic spraying device 10 is turned off. As a result, the electric field between the nozzle and the skin disappears, and the surface of the skin is immobilized with an electric charge. Consequently, the adhesivity of the coating is further improved.

Although the above description has been directed to a porous coating composed of a fiber deposit as a coating, the form of the coating is not limited to this, and a continuous coating without pores may be formed, or a porous coating having a form other than the fiber deposit, for example, a porous coating in which multiple through-holes are formed irregularly or regularly in the continuous coating, i.e., a discontinuous coating may be formed. As described above, any shape of the coating can be formed by controlling the viscosity of the spraying composition, the distance between the nozzle and the skin, the voltage applied to the nozzle, and the like.

The distance between the nozzle and the skin also depends on the voltage applied to the nozzle, but in order to successfully form the coating, a distance of 50 mm or more and 150 mm or less is preferred for. The distance between the nozzle and the skin can be measured by a commonly used non-contact sensor or the like.

Whether or not the coating formed by the electrostatic spraying method is porous, the basis weight of the coating is preferably 0.1 $g/m^2$ or more, more preferably 1 $g/m^2$ or more. Further, it is preferable to be 30 $g/m^2$ or less, and more preferable to be 20 $g/m^2$ or less. For example, the basis weight of the coating is preferably 0.1 $g/m^2$ or more and 30 $g/m^3$ or less, and more preferably 1 $g/m^2$ or more, and 20 $g/m^2$ or less. By setting the basis weight of the coating in this manner, the adhesivity of the coating can be improved. The electrostatic spraying step of forming a coating by electrostatically spraying the composition directly onto the skin means a step of electrostatically spraying onto the skin to form a coating. The step of electrostatically spraying a composition to a location other than the skin to produce a sheet of fibers and applying the sheet to the skin differs from the electrostatically spraying step above.

Next, the Step B) will be described, step B) is a step of applying a powder-containing cosmetic to the coating formed in Step A) by a method other than electrostatic spraying.

Examples of the powders used in the cosmetics of Step B) include a coloring pigment, a constitutive pigment, a pearl pigment, an organic powder. The coloring pigment includes an inorganic coloring pigment, an organic coloring pigment, and an organic dye, and one or more of these can be used.

Specific examples of the inorganic coloring pigment include an inorganic color pigment such as red iron oxide, iron hydroxide, iron titanate, yellow iron oxide, black iron oxide, carbon black, dark blue, ultramarine blue, dark blue titanium oxide, black titanium oxide, sintered products of titanium and titanium oxide, manganese violet, cobalt violet, chromium oxide, chromium hydroxide, cobalt oxide, cobalt titanate; an inorganic white pigment such as titanium oxide, zinc oxide, calamine, zirconium oxide, magnesium oxide, cerium oxide, aluminum oxide, and composites thereof. One or more of these can be used.

Among these, at least one or more selected from the group consisting of iron oxide, titanium oxide, and zinc oxide are preferable, and one or more selected from the group consisting of titanium oxide, zinc oxide, red iron oxide, yellow iron oxide, and black iron oxide are more preferable.

Examples of the organic pigment and the organic dye include organic for pigments such as red No. 3, red No. 102, red No. 104, red No. 106, red No. 201, red No. 202, red No. 204, red No. 205, red No. 220, red No. 226, red No. 227, red No. 228, red No. 230, red No. 401, red No. 405, red No. 505, orange No. 203, orange No. 204, orange No. 205, yellow No. 4, yellow No. 5, yellow No. 401, blue No. 1, and blue No. 404; and organic dyes such as β-carotene, caramel, and paprika dyes. In addition, a polymer coated with cellulose, polymethacrylic acid ester, or the like may be used. Of these, it is preferable to contain at least red No. 102.

Examples of the constitutive pigment include barium sulfate, calcium sulfate, magnesium sulfate, magnesium carbonate, calcium carbonate, talc, mica, kaolin, sericite, silicic acid, anhydrous silicic acid, aluminum silicate, magnesium silicate, magnesium aluminum silicate, calcium silicate, barium silicate, strontium silicate, metal tungstate, hydroxyapatite, vermiculite, clay, bentonite, montmorillonite, hectorite, smectite, zeolite, ceramic powder, phosphorous acid, alumina, silica, aluminum hydroxide, boron nitride, synthetic mica, synthetic sericite, metal soap, barium sulfate-treated mica, and the like. One or more of these can be used.

Among these, barium sulfate, calcium carbonate, mica, anhydrous silicic acid, talc, boron nitride, and synthetic mica are preferably included.

Examples of the pearl pigment (glittering powders) include fish foil, titanium oxide-coated mica (mica titanium), bismuth oxychloride, titanium oxide-coated bismuth oxychloride, titanium oxide-coated talc, titanium oxide-coated color mica, (titanium oxide/iron oxide)-coated mica, microparticulate titanium oxide-coated mica titanium, microparticulate zinc oxide-coated mica titanium, organic pigment-treated mica titanium, low-order titanium oxide-coated mica, titanium oxide-coated synthetic mica, titanium oxide-coated platy silica, hollow plate-like titanium oxide, iron oxide-coated mica, platy iron oxide (MIO), aluminum flakes, stainless flakes, titanium oxide-coated alumina plate alumina, glass flakes, a titanium oxide-coated glass flakes, pearl shell, gold foil, gold vapor-coated resin film, metal vapor-coated resin film. One or more thereof can be used.

Examples of the organic powder include a silicone rubber powder, a silicone resin-coated silicone rubber powder, polymethylsilsesquioxane, a polyamide powder, a nylon powder, a polyester powder, a polypropylene powder, a polystyrene powder, a polyurethane powder, a vinyl resin powder, a urea resin powder, aphenolic resin powder, a fluorine resin powder, a silicon resin powder, an acrylic resin powder, a melamine resin powder, a polycarbonate resin, a divinylbenzene-styrene copolymer, a silk powder, a wool powder, a cellulose powder, a long-chain alkyl phosphoric acid metal salt, an N-mono long chain alkyl acyl basic amino acid, and a composite thereof. One or more of these can be used.

Among these, it is preferable to contain a cellulose powder, a silicone rubber powder, a silicone resin-coated silicone rubber powder, polymethylsilsesquioxane, an acrylic resin powder, or a nylon powder.

Any of the powders used in the present invention can be used as it is, and one or more of them can be used after subjected to hydrophobic treatment. The hydrophobic treatment is not limited as long as it is applied to usual cosmetic powders, and dry treatment, wet treatment, or the like may be performed using a surface treatment agent such as a fluorine compound, a silicone compound, a metal soap, an amino acid compound, lecithin, an alkylsilane, an oil agent, or an organic titanate.

Specific examples of the surface treatment agent include: a fluorine-based compound such as a perfluoropolyether, a perfluoroalkyl phosphate ester, a perfluoroalkyloxy silane, a fluorine-degeneration silicone; a silicone-based compound such as a dimethylpolysiloxane, a cyclic silicone, a single-terminal or a double-terminal trialkoxy group-modified organopolysiloxane, a crosslinked silicone resin, a fluorine-modified silicone resin, and an acryl-modified silicone; a metal soap such as aluminum stearate, zinc stearate, and magnesium stearate; proline, hydroxyproline, alanine, glycine, sarcosine, glutamic acid, aspartic acid, lysine and a derivative thereof; lecithin, hydrogenated lecithin, an alkyl silane such as methyltriraethoxysilane, ethyltrimethoxysilane, hexyltrimethoxysilane, octyltrimethoxysilane, octyltriethoxysilane; an oil agent such as polyisobutylene, wax and a fat; an organic titanate such as isopropyltitanium triisostearate.

As the powder used in the present invention, one or more of them may be further subjected to hydrophilic treatment. The hydrophilic treatment is not limited as long as it is applied to a normal cosmetic powder.

Examples of the powder include a plant-based polymer such as gum arabia, tragacanth, locust bean gum (carobgum), guar gum, carrageenan, pectin, agar, cousin seed (marmelo), starch (rice, corn, pepper, wheat), algelloid, tranche gum, locust bean gum; a microbial-based polymer such as xanthan gum, dextran, succinoglucan, pullulan; and an animal-based polymer such as collagen, casein, albumin, deoxyribonucleic acid (DNA) and a salt thereof; a starch-based polymer such as a carboxymethyl starch, a methyl hydroxypropyl starch; a cellulose-based polymer such as methyl cellulose, ethyl cellulose, methyl hydroxypropyl cellulose, carboxymethyl cellulose, hydroxypropyl cellulose, nitrocellulose, sodium cellulose sulfate, sodium carboxymethyl cellulose, crystalline cellulose, a cellulose-terminated cellulosic polymer; an alginic acid-based polymer such as sodium alginate and a propylene glycol alginate esters a vinyl polymer such as polyvinyl methyl ether, polyvinyl pyrroldone and a carboxyvinyl polymer; a polyoxyethylene polymer such as polyethylene glycol and polyethylene glycol silane; a polyoxyethylene polyoxypropylene copolymer-based polymer; an acrylic polymer such as sodium polyacrylate, polyethylene acrylate and polyacrylic acid amide; and an inorganic silicic compound such as silica.

As the powder, as long as it is a powder normally used in cosmetics, a powder having a shape such as a sphere, a plate, a needle, or an indefinite shape, a particle diameter such as a fume shape, a fine particle shape, or a pigment grade, a particle structure such as porous or non-porous, or the like can be used.

The average particle diameter of the powder is preferably 0.001 μm or more and 200 μm or less, more preferably 0.01 μm or more and 50 μm or less, further more preferably 0.02 μm or more and 20 μm or less, and even more preferably 0.05 μm or more and 10 μm or less, from the viewpoint that the powder adheres uniformly to the hills, hides, and pores of the skin and provides a natural cosmetic feeling.

In the present invention, the average particle size of the powder is measured by electron-microscopy, laser diffraction/scattering particle size distributor. Specifically, for the laser diffraction/scattering method, ethanol is used as the dispersion medium and measured by a laser diffractive particle size distribution meter (e.g., Seishin Corporation, LMS-353). When the powder is subjected to hydrophobic treatment or hydrophilic treatment, the average particle diameter and the content of component (c) mean the average particle diameter and the mass including the hydrophobic treatment or the hydrophilic treatment agent.

One or more powders can be used, and the content differs depending on the form of the cosmetic, but from the viewpoint of the finish, 1 mass % or more is preferable, 3 mass % or more is more preferable, 5 mass % or more is even more preferable; 99 mass % or less is preferable, 95 mass % or less is more preferable, and 90 mass % or less is even more preferable. The content of the powder is preferably 1 mass % or more and 99 mass % or less, more preferably 3 mass % or more and 95 mass % or less, and even more preferably 5 mass % or more and 90 mass % or less in the cosmetic.

The mass ratio of the coloring pigment to the total powder (coloring pigment/component (c)) is preferably 0.2 or more, more preferably 0.3 or more, further more preferably 0.4 or more, and even more preferably 1.0 or less from the viewpoint of the finish and the excellence in cosmetic durability because the powder-containing cosmetic is hard to collapse even after a lapse of time.

The type of the cosmetic used in Step B) is not particularly limited as long as it is a powder-containing cosmetic, and can be applied as a makeup cosmetic such as a makeup base, a foundation, a concealer, a blush, an eye shadow, a mascara, an eye liner, an eye brow, an overcoat agent, a lipstick; or an UV protective cosmetic such as a sunscreen emulsion, a sunscreen cream. Among these, a makeup base, a foundation, a concealer, a sunscreen emulsion, and a sunscreen cream are more preferable.

The form of the cosmetic is net particularly limited, and it may be a powdered cosmetic, a solidified powder cosmetic, a liquid cosmetic, an oily cosmetic, an emulsified cosmetic, or an oily solid cosmetic.

Components other than the powder contained in the powder-containing cosmetic used in Step B) include an oil agent (including a liquid oil and a solid oil), an emulsifier, a water-soluble polymer, a perfume, a repellent, an antioxidant, a stabilizer, a preservative, a thickener, a pH adjustor, a blood circulation promotor, various vitamins, a cooling agent, an antiperspirant, a disinfectant, a skin activator, a moisturizer, and the like.

The application of the cosmetic in Step B) may be performed by an ordinary application method other than electrostatic spraying depending on the type of the cosmetic, and for example, application may be performed by spreading or holding the cosmetic by using a finger or a palm, spreading the cosmetic or pressing the applied site by using a dedicated tool.

Further, it is preferable to carry out step (C) of forming a coating by electrostatically spraying the composition containing components (a) and (b) on the cosmetic coating after Step (B) (Step C)) from the viewpoint that the powder-containing cosmetic can be easily and completely removed only by peeling with a finger without using a cleansing agent, that color transfer and adhesion of the powder-containing cosmetic to the clothes etc. are prevented, and that makeup collapse derived from the powder-containing cosmetic is prevented.

That is, if a porous coating, more preferably a coating composed of a fiber deposit, is formed on the cosmetic coating obtained in Step B) by electrostatic spraying, color transfer and powder adhesion of the powder-containing cosmetic to the clothes are effectively prevented, and as a result, the cosmetic quality improves. Further, the peeling property at the time of peeling the cosmetic coating with a finger etc. is improved, and the coating can be easily and completely peeled off from the skin.

Here, Step C) can be performed in the same manner as Step A) except that the surface to which the powder-containing cosmetic is applied is electrostatically sprayed.

In the present invention, Step C) may be followed by a liquid agent application step in which a liquid agent containing one or more selected from the group consisting of water, a polyol and an oil in a liquid state at 20° C. is applied to the skin by a method other than electrostatic spraying. In addition, by performing the liquid agent application step by a method other than electrostatic spraying immediately after Step C), in particular, the coating formed in the electrostatic spraying step becomes easily adaptable to the skin by the liquid agent, and the coating adheres to the skin highly and the transparency is further improved. Then, an unevenness is less likely to be made between the edge of the coating and the skin, which also improves the adhesivity between the coating and the skin. Suitably, when the coating is a porous coating composed of a fiber deposit, it exerts high adhesivity to the skin despite the high porosity, and a large capillary force is apt to occur. Further, when the fibers are fine, it is easy to make the porous coating have a high specific surface area.

Although the present invention has been described above with reference to its preferred embodiment, the present invention is not limited to the embodiments described above. For example, in the embodiment described above, a person who wants to form a coating on his/her skin holds the electrostatic spraying device 10 and generates an electric field between the nozzle of the device 10 and his/her skin, but as long as an electric field is generated between the two, it is not necessary for him or her to hold the electrostatic spraying device 10.

With respect to the embodiments described above, the present invention further discloses the following methods for producing a cosmetic coating.

<1> A method for producing a cosmetic coating on a skin surface, the method comprising
Step A) of electrostatically spraying a composition comprising
component (a) one or more volatile substances selected from the group consisting of water, an alcohol and a ketone, and
component (b) a polymer having a film-forming ability directly onto the skin to form a coating on the skin surface; and
Step B) of subsequently applying a powder-containing cosmetic on the formed coating.

<2> The method according to <1>, wherein the cosmetic in Step B) is applied by a method other than electrostatic spraying.

<3> The method according to <1> or <2>, further comprising Step C) of electrostatically spraying a composition containing component (a) and component (b) onto the cosmetic coating after Step B).

<4> The method according to any one of the <1> to <3>, wherein the coating formed by electrostatic spraying in the Steps A) and C) is a porous coating.

<5> The method according to any one of <1> to <4>, wherein the electrostatic spraying Steps A) and C) are steps of electrostatically spraying the composition onto the skin by using an electrostatic spraying device to form a coating composed of a fiber deposit,
and the electrostatic spraying device comprises a container containing the composition, a nozzle for discharging the composition, a supply device for supplying the composition contained in the container to the nozzle, and a power supply for applying a voltage to the nozzle.

<6> The method according to any one of <1> to <5>, wherein the (a) volatile substance has a vapor pressure at 20° C. of 0.01 kPa or more and 106.66 kPa or less, preferably 0.13 kPa or more and 66.66 kPa or less, more preferably 0.67 kPa or more and 40.00 kPa or less, and even more preferably 1.33 kPa or more and 40.00 kPa or less.

<7> The method according to any one of <1> to <5>, wherein the (a) volatile substance is an alcohol, and the alcohol is a monovalent chain aliphatic alcohol, a monovalent cyclic aliphatic alcohol, or a monovalent aromatic alcohol, and selected from the group consisting of ethanol, isopropyl alcohol, butyl alcohol, phenylethyl alcohol, propanol, pentanol, and the like is used, and one or more selected from these alcohols are used.

<8> The method for producing a cosmetic coating according to any one of <1> to <7>, wherein, as the ketone among the (a) volatile substance, acetone, methyl ethyl ketone, methyl isobutyl ketone, or the like is used, and one of these ketones is used alone or in combination of two or more.

<9> The method according to any one of <1> to <8>, wherein the (a) volatile substance is one or more selected from the group consisting of ethanol, isopropyl alcohol, butyl alcohol, and water, preferably one or more selected from the group consisting of ethanol and butyl alcohol, and further more preferably a volatile substance at least containing ethanol, and even more preferably a volatile substance at least containing ethanol, and the content of ethanol in the volatile substance is 50 mass % or more and 100 mass % or less.

<10> The method according to any one of <1> to <9>, wherein the polymer having a film-forming ability is water-soluble, and the water-soluble polymer having a film-forming ability is mucopolysaccharide such as pullulan, hyaluronic acid, chondroitin sulfate, poly-γ-glutamic acid, a modified corn starch, β-glucan, gluco-oligosaccharide, heparin, keratosulfuric acid; a natural polymer such as cellulose, pectin, xylan, lignin, glucomannan, galacturonic acid, thyrium seed gum, tamarind seed gum, arabic gum, tragacanth gum, soy water-soluble polysaccharide, alginic acid, carrageenan, laminaran, agar (agarose), fucoidan, methyl cellulose, hydroxypropyl cellulose, hydroxypropylmethyl cellulose; a synthetic polymer such as partially saponified polyvinyl alcohol (where a crosslinking agent is not used), low-saponified polyvinyl alcohol, polyvinyl pyrrolidone (PVP), polyethylene oxide, sodium polyacrylate, one or more of which may be used.

<11> The method according to any one of <1> to <10>, wherein the polymer having a film-forming ability is water-insoluble, and the water-insoluble polymer having a film-forming ability is a fully saponified polyvinyl alcohol which can be insolubilized after the formation of a coating, a partially saponified polyvinyl alcohol which can be crosslinked in combination with a crosslinking agent after the formation of a coating, an oxazoline-modified silicone (e.g., poly(N-propanoylethyleneimine) graft-dimethylsiloxane/γ-aminopropylmethylsiloxane copolymer), polyvinylacetal diethylaminoacetate, Zein (main component of corn protein), polyester, polylactic acid (PLA), an acrylic resin (e.g., a polyacrylonitrile resin, a polymethacrylic acid resin), a polystyrene resin, a polyvinyl butyral resin, a polyethylene terephthalate resin, a polybutylene terephthalate resin, a polyurethane resin, a polyamide resin, a polyamideimide resin, one or more of which may be used.

<12> The method according to any one of <1> to <11>, wherein component, (b) is preferably one or more selected from the group consisting of a fully saponified or partially saponified polyvinyl alcohol, a polyvinyl butyral resin, a polyurethane resin, an oxazoline-modified silicone, a water-soluble polyester, and Zein, and more preferably one or more selected from the group consisting of a polyvinylbutyral resin and a polyurethane resin.

<13> The method according to any one of <1> to <12>, wherein component (a) is a volatile substance at least containing ethanol, and component (b) is one or more selected from the group consisting of a polyvinyl butyral resin and a polyurethane resin.

<14> The method according to any one of <1> to <13>, wherein the content of component (a) in the composition is 30 mass % or more, preferably 55 mass % or more, more preferably 60 mass % or more, and 98 mass % or less, preferably 96 mass % or less, more preferably 94 mass % or less, and 30 mass % or more and 98 mass % or less, preferably 55 mass % or more and 96 mass % or less, more preferably 60 mass % or more and 94 mass % or less.

<15> The method according to any one of <1> to <14>, wherein the content of component (b) in the composition is 2 mass % or more, preferably 4 mass % or more, more preferably 6 mass % or more, and 30 mass % or less, preferably 45 mass % or less, even more preferably 40 mass % or less, and 2 mass % or more and 50 mass % or less, preferably 4 mass % or more and 45 mass % or less, even more preferably 6 mass % or more and 40 mass % or less.

<16> The method according to anyoneof<1> to <15>, wherein the composition has a viscosity at 25° C. of 1 mPa·s or more, preferably 10 mPa·s or more, more preferably 50 mPa·s or more, and preferably 5,000 mPa·s or less, more preferably 1,500 mPa·s or less, and 1 mPa·s or more and 5,000 mPa·s or less, more preferably 10 mPa·s or more and 2,000 mPa·s or less, and even more preferably 50 mPa·s or more and 1,500 mPa·s or less.

<17> The method according to any one of <1> to <16>, wherein either the composition comprises only component (a) and component (b), or the composition comprises other components in addition to component (a) and component (b), and as the other component(s), a plasticizer of the (b) polymer having a film-forming ability, an oil agent, a surfactant, a UV protective agent, a perfume, a repellent, an antioxidant, a stabilizer, a preservative, and various vitamins are used.

<18> The method according to <17>, wherein when the composition contains other component(s), the content of the other component(s) is preferably 0.1 mass % or more and 30 mass % or less, and more preferably 0.5 mass % or more and 20 mass % or less.

<19> The method according to any one of <1> to <18>, wherein the electrostatic spraying is performed by an electrostatic spraying device, the electrostatic spraying device comprises a nozzle, and
the nozzle is made of a conductive material such as metal or a non-conductive material such as plastic, rubber, ceramic, or the like, and the nozzle has a shape such that the composition may be discharged from the tip thereof.

<20> The method according to any of <1> to <19>, wherein the electrostatic spraying is performed by an electrostatic spraying device, the electrostatic spraying device comprises a nozzle and a housing, the nozzle is disposed in one of longitudinal edges of the housing, and the nozzle is disposed such that a discharge direction of the composition coincides with the longitudinal direction of the housing and the nozzle protrudes toward the skin side.

<21> The method according to anyone of <1> to <20>, which forms a fiber by stretching and deforming the sprayed composition by a potential difference, while volatilizing a volatile substance (a solvent), from a droplet to solidify a polymer (a solute having a film-forming ability).

<22> The method according to any one of <1> to <21>, wherein the electrostatic spraying is performed by an electrostatic spraying device the electrostatic spraying device comprises a nozzle, the distance between the nozzle and the skin is 50 mm or more and 150 mm or less.

<23> The method according to any one of <1> to <22>, wherein the basis weight of the coating formed by the electrostatic spraying method is preferably 0.1 g/m$^2$ or more, more preferably 1 g/m$^2$ or more, and preferably 30 g/m$^2$ or less, more preferably 20 g/m$^2$ or less, and the basis weight of the coating is preferably 0.1 g/m$^2$ or more and 30 g/m$^2$ or less, and more preferably 1 g/m$^2$ or more and 20 g/m$^2$ or less.

<24> The method according to any one of <1> to <23>, wherein the powder used in the cosmetic of step B) is one or more selected from the group consisting of a coloring pigment, a constitutive pigment, a pearl pigment, and an organic powder, and preferably one or more selected from the group consisting of an inorganic coloring pigment, an organic coloring pigment, an organic coloring stuff, a constitutive pigment, a pearl pigment, and an organic powder.

<25> The method according to wherein the inorganic coloring pigment is one or more selected from the group consisting of an inorganic colored pigment such as red iron oxide, iron hydroxide, iron titanate, yellow iron oxide, black iron oxide, carbon black, dark blue, ultramarine blue, dark blue titanium oxide, black titanium oxide, sintered titanium/titanium oxide, manganese violet, cobalt violet, chromium oxide, chromium hydroxide, cobalt oxide, cobalt titanate; and inorganic white pigment such as titanium oxide, zinc oxide, caramin, zirconium oxide, magnesium oxide, cerium oxide, aluminum oxide, and composites thereof, and one or more selected from the group consisting of iron oxide, titanium oxide and zinc oxide is preferable, and one or more selected from the group consisting of titanium oxide, zinc oxide, red iron oxide, yellow iron oxide and black iron oxide.

<26> The method according to <24>, wherein the organic coloring pigment/organic coloring stuff is an organic tar-based pigment such as red No. 3, red No. 102, red No. 104, red No. 106, red No. 201, red No. 202, red No. 204, red No. 205, red No. 220, red No. 226, red No. 227, red No. 228, red No. 230, red No. 401, red No. 405, red No. 505, orange No. 203, orange No. 204, yellow No. 205, yellow No. 4, yellow No. 5, yellow No. 401, blue No. 1, blue No. 404; and an organic coloring stuff such as β-carotene, caramel, and papula.

<27> The method according to <24>, wherein the constitutive pigment is one or more selected from the group consisting of barium sulfate, calcium sulfate, magnesium sulfate, magnesium carbonate, calcium carbonate, talc, mica, kaolin, sericite, silicic acid, anhydrous silicic acid, aluminum silicate, magnesium silicate, magnesium aluminum silicate, calcium silicate, barium silicate, strontium silicate, metal tungstate, hydroxyapatite, vermiculite, clay, bentonite, montmorillonite, hectite, smectite, zeolite, ceramic powder, dibasic calcium phosphate, alumina, silica, aluminum hydroxide, boron nitride, synthetic mica, synthetic sericite, metal soap, barium sulfate and barium sulfate-treated mica; preferably one or more selected from the group consisting of barium sulfate, calcium carbonate, mica, anhydrous silicic acid, talc, boron nitride and synthetic mica.

<28> The method according to <24>, wherein the pearl pigment (bright powder) is one or more selected from the group consisting of fish foil, titanium oxide-coated mica (mica titanium), bismuth oxychloride, titanium oxide-coated bismuth oxychloride, titanium oxide-coated talc, titanium oxide-coated coloring mica, titanium oxide/iron oxide coated mica, fine particle titanium oxide-coated titanium mica, fine particle zinc oxide-coated titanium mica, organic pigment-treated titanium mica, low order titanium oxide-coated mica, titanium oxide-coated synthetic mica, titanium oxide-coated platy silica, hollow platy titanium oxide, iron oxide-coated mica, platy iron oxide (MIO), aluminum flake, stainless flake, titanium oxide-coated platy alumina, glass flake, titanium oxide-coated glass flake, pearlescent shell, gold foil, a gold vapor-deposited resin film, and a metal vapor-deposited resin film.

<29> The method according to <24>, wherein the organic powder is one or more selected from the group consisting of a silicone rubber powder, a silicone resin-coated silicone rubber powder, polymethylsilsesquioxane, a polyamide powder, a nylon powder, a polyester powder, a polypropylene powder, a polystyrene powder, a polyurethane powder, a vinyl resin powder, a urea resin powder, aphenolic resin powder, a fluorine resin powder, a silicon resin powder, an acrylic resin powder, a melamine resin powder, a polycarbonate resin, a divinylbenzene-styrene copolymer, a silk powder, a wool powder, a cellulose powder, a long-chain alkyl phosphoric acid metal salt, N-mono long-chain alkylacyl basic amino acid and a composite thereof, preferably one or more selected from the group consisting of a cellulose powder, a silicone rubber powder, a silicone resin coated silicone rubber powder, polymethylsilsesquioxane, an acrylic resin powder and a nylon powder.

<30> The method according to any one of <24> to <29>, wherein the powder is a powder that has been subjected to hydrophobic treatment, and is preferably a powder that has been subjected to hydrophobic treatment selected from the group consisting of a fluorine compound, a silicone compound, a metal soap, an amino acid compound, lecithin, an alkylsilane, an oil agent, and an organic titanate.

<31> The method according to any one of <24> to <29>, wherein the powder is a powder that has been subjected to hydrophilic treatment.

<32> The method according to anyone of <1> to <31>, wherein the average particle diameter of the powder is preferably 0.001 μm or more and 200 μm or less, more preferably 0.01 μm or more and 50 μm or less, more preferably 0.02 μm or more and 20 μm or less, and even more preferably 0.05 μm or more and 10 μm or less is more preferably <1> to <31>.

<33> The method according to any one of <1> to <32>, wherein the content of the powder in the cosmetic is 1 mass % or more, preferably 3 mass % or more, more preferably 5 mass % or more, and 99 mass % or less, preferably 95 mass % or less, more preferably 90 mass % or less, and preferably 1 mass % or more and 99 mass % or less, more preferably 3 mass % or more and 95 mass % or less, and even preferably 5 mass % or more and 90 mass % or less.

<34> The method according to any one of <1> to <33>, wherein the mass ratio of the coloring pigment to the total powder, (coloring pigment/component (c)), in the cosmetic is preferably 0.2 or more, more preferably 0.3 or more, and even more preferably 0.4 or more, and preferably 1.0 or less.

<35> The method according to anyone of <1> to <34>, wherein the cosmetic is a makeup cosmetic such as a makeup base, a foundation, a concealer, a blush, an eye shadow, a mascara, an eye liner, an eye brow, a lipstick; or an UV protective cosmetic such as a sunscreen emulsion and a sunscreen cream; and preferably a makeup base, a foundation, a concealer, a sunscreen emulsion or a sunscreen cream.

<36> The method according to any one of <1> to <35>, wherein the cosmetic is a powder cosmetic, a solid powdered cosmetic, a liquid cosmetic, an oily cosmetic, an emulsified cosmetic, or an oily solid cosmetic.

<37> The method according to any one of <1> to <36>, wherein the cosmetic further comprises at least one or more selected from the group consisting of an oil (including a liquid oil and a solid oil), an emulsifier, a water-soluble polymer, a perfume, a repellent, an antioxidant, a stabilizer, a preservative, a thickener, a pH adjustor, a blood circulation accelerator, various vitamin, a cooling sensation agent, an antiperspirant, a skin activator, and a humectant.

<38> The method according to any one of <1> to <37>, wherein the content of component (a) is 30 mass % or more and 98 mass % or less in the composition, and the content of component (b) is 2 mass % or more and 50 mass % or less in the spraying composition.

<39> The method according to any one of <1> to <37>, wherein the content of component (a) is 55 mass % or more and 90 mass % or less in the composition, and the content of component (b) is 4 mass % or more and 45 mass % or less in the spraying composition.

<40> The method according to any one of <1> to <37>, wherein the content of component (a) is 60 mass % or more and 94 mass % or less in the composition, and the content of component (b) is 6 mass % or more and 40 mass % or less in the spraying composition.

<41> The method according to any one of <1> to <40>, wherein component (a) is a volatile substance at least containing ethanol, and component (b) is one or more selected from the group consisting of a polyvinyl butyral resin and a polyurethane resin.

EXAMPLES

The present invention will be explained in more detail by means of the following examples. However, the scope of the present invention is not limited to these examples. Unless otherwise specified, "%" means "mass %".

[Test 1]

Examples 1 to 11

(1) Preparation of Spraying Compositions

The composition shown in Table 1 was used for spraying.

(2) Powder-Containing Cosmetics

Commercially available makeup cosmetics shown in Table 2 were used.

(3) Electrostatic Spraying (Step A))

An electrostatic spraying device 10 having the configuration shown in FIG. 1 and having the appearance shown in FIG. 2 was used, and an electrostatic spraying method was performed onto the cheeks of a person for 20 seconds. The conditions of the electrostatic spraying method were as follows.

Applied voltage: 10 kV
Distance between nozzle and skin: 100 mm
Volume of spraying composition discharged: 5 mL/h
Environment: 25° C., 30% RH The electrostatic spraying device formed a porous coating composed of a fiber deposit on the skin surface. The coating was a circle approximately 4 cm in diameter and its mass was approximately 5.5 mg. The fiber thickness measured by the method described above was 506 nm.

(4) Powder-Containing Cosmetic Coating (Step B))

An emulsion is applied onto the coating formed in the electrostatic step A) to adapt the coating to the skin, and thereafter, an appropriate amount of a target powder cosmetic is applied.

(5) Electrostatic Spraying (Step C))

Electrostatic spraying was performed onto the skin to which the powder-containing cosmetic was applied under the same conditions as in the above-mentioned electrostatic spraying of Step A).

Comparative Examples 1 to 3

Without the electrostatic spraying of Step A), the application of the powder-containing cosmetic and then the electrostatic spraying of Step C) were carried out.

[Evaluation]

(1) Residual Properties of Powder on the Skin when Powder Cosmetics Adhered to the Skin were Peeled Off After each cosmetic was applied to the skin according to the procedure of Table 1 by an expert panelist, the residual property of the powder when the powder cosmetic adhered to the skin was peeled off from the skin in a coating state without using a cleansing agent was evaluated. The residual property was subjected to sensory evaluation by the following criteria. Results are presented as the mean of five evaluators.

[Evaluation Criteria]
4: No powder of the powder cosmetic adheres to the skin after peeling.
3: Powder of powder cosmetic is not very adhered to the skin after peeling.
2: The powder of the powder cosmetic slightly adheres to the skin after peeling.
1: The powder of the powder cosmetic remains attached to the skin after peeling.

(2) How the Coating is Removed when the Powder Cosmetic that has Adhered to the Skin is Peeled Off After each cosmetic was applied to the skin according to the procedure of Table 1, the powder cosmetic attached to the skin was peeled off from the skin in a coated state without using a cleansing agent by a specialist panelist, and the peeling off of the powder cosmetic and the coating was evaluated. The manner of peeling was subjected to sensory evaluation by the following criteria. Results are presented as the mean of five evaluators.

[Evaluation Criteria]
4: The powder cosmetic and the coating can be uniformly and integrally removed when peeled from the skin.
3: The powder cosmetic and the coating can be removed slightly integrally when peeled from the skin.
2: When peeled from the skin, the powder cosmetic and the coating can be removed in a blurred state.
1: The powder cosmetic and the coating cannot be removed in a coated state when peeled from the skin.

(3) Lack of Makeup Collapse after the Elapse of Time

Each cosmetic was applied to the skin by a specialist panelist according to the procedure of Table 1, and the state of makeup collapse after 5 hours was evaluated. The makeup collapse was judged by the sensory evaluation according to the following criteria. Results are presented as the mean of 5 panelists.

[Evaluation Criteria]
4: After 5 hours, no makeup collapse is observed at all.
3: After 5 hours, makeup collapse is not observed.
2: After the elapse of 5 hours, makeup collapse is observed.
1: After 5 hours, makeup collapse is observed.

Evaluation results are given in Table 3.

TABLE 1

| Component | Purify | Spraying Composition 1 | Spraying composition 2 | Spraying composition 3 |
|---|---|---|---|---|
| Polyvinyl butyral *1 | 100% | 15.00 | | |
| Polyvinyl acetal diethylaminoacetate*2 | 100% | | 15.00 | |
| Dry methacrylic acid copolymer LD*3 | 100% | | | 15.00 |
| Ethanol*4 | 99.5% | 80.00 | 80.00 | 80.00 |
| Di(phytosteryl/octytdodecyl)*5 lauroyl glutamate | 100% | 5.00 | 5.00 | 5.00 |
| Total | | 100.00 | 100.00 | 100.00 |

*1: S-lec B BM-1 (Sekisui Chemical Co., Ltd.)
*2AEA (Mitsubishi Chemical Corporation)
*3Eudragit L100-55 (Evonic Japan Co., Ltd.)
*499.5% ethanol
*5Eldew PS-203 (Ajinomoto Co., Inc.)

TABLE 2

| | Makeup cosmetic A | Makeup cosmetic B | Makeup cosmetic C | Makeup cosmetic D |
|---|---|---|---|---|
| Commercial name | Sofina Primavista Powder foundation UV | Sofina Primavista Cream foundation | Sofina Primavista Liquid foundation | Sofina Primavista Concealer |
| Content of powder | 25.0% | 23.0% | 24.8% | 17.6% |
| Content of coloring pigment | 11.6% | 10.8% | 10.1% | 9.1% |

TABLE 3

| | | Example | | | | | | | | | | | Comparative Example | | |
|---|---|---|---|---|---|---|---|---|---|---|---|---|---|---|---|
| | | 1 | 2 | 3 | 4 | 5 | 6 | 7 | 8 | 9 | 10 | 11 | 1 | 2 | 3 |
| I | Spraying composition | 1 | 2 | 1 | 2 | 3 | 1 | 1 | 1 | 1 | 2 | 1 | — | — | — |
| II | Makeup cosmetic | A | A | A | A | A | B | C | D | A | A | A + B | A | A | B |
| III | Spraying composition | — | — | 1 | 2 | 3 | 1 | 1 | 1 | 2 | 1 | 1 | 1 | 2 | 1 |
| | Residual properties of powder on the skin when powder cosmetics adhered to the skin were peeled off | 4.0 | 4.0 | 4.0 | 4.0 | 4.0 | 4.0 | 4.0 | 4.0 | 4.0 | 4.0 | 4.0 | 1.0 | 1.0 | 1.0 |
| | How the coating is removed when the powder cosmetic that has adhered to the skin is peeled off | 3.4 | 3.2 | 4.0 | 4.0 | 3.2 | 4.0 | 4.0 | 4.0 | 4.0 | 3.8 | 4.0 | 1.4 | 1.0 | 1.0 |
| | Lack of makeup collapse after the elapse of time | 3.8 | 3.4 | 4.0 | 3.8 | 3.4 | 4.0 | 4.0 | 4.0 | 4.0 | 3.8 | 4.0 | 1.2 | 1.0 | 1.0 |

EXPLANATION OF SYMBOLS

10 Electrostatic spray equipment
11 Low-voltage power supply
12 High-voltage power supply
13 Auxiliary electrical circuit
14 Microgear pump
15 Container
16 Nozzle
17 Pipe
18 Flexible pipe
19 Current limit resistor
20 Housing

The invention claimed is:

1. A method for producing a cosmetic coating on a skin surface, the method comprising
   (A) electrostatically spraying a composition comprising
   component (a) one or more volatile substances selected from the group consisting of water, an alcohol and a ketone, and
   component (b) a polymer having a film-forming ability directly onto the skin to form a coating comprising a deposit of continuous fibers on the skin surface; and
   (B) subsequently applying by a method other than electrostatic spraying a powder-containing cosmetic on the formed coating,
   wherein:
   said obtained cosmetic coating allows removing or peeling off by finger,
   said continuous fibers have a length which is at least 100 times greater than their thickness, and
   the content of the component (a) is 30 mass % or more and 98 mass % or less in the composition, and the content of the component (b) is 2 mass % or more and 50 mass % or less in the composition.

2. The method according to claim 1, further comprising
   (C) electrostatically spraying a composition containing the component (a) and component (b) onto the cosmetic coating after (B).

3. The method according to claim 2, wherein the coatings produced by the electrostatic spraying in (A) and (C) are porous.

4. The method according to claim 2, wherein each of (A) and (C) comprises electrostatically spraying the composition onto the skin by using an electrostatic spraying device to form a coating composed of a fiber deposit,
   and the electrostatic spraying device comprises a container containing the composition, a nozzle for discharging the composition therefrom, a supply device for supplying the composition contained in the container to the nozzle, and a power supply for applying a voltage to the nozzle.

5. The method according to claim 1, wherein the component (a) is one or more members selected from the group consisting of ethanol, isopropyl alcohol, butyl alcohol, and water.

6. The method according to claim 1, wherein the component (a) is a volatile substance at least comprising ethanol.

7. The method according to claim 6, wherein the component (a) is a volatile substance at least comprising ethanol, and the content of the ethanol in the volatile substance is 50 mass % or more and 100 mass % or less.

8. The method according to claim 1, wherein the component (b) is one or more members selected from the group consisting of a fully saponified or partially saponified polyvinyl alcohol, a polyvinyl butyral resin, a polyurethane resin, an oxazoline-modified silicone, a water-soluble polyester, and Zein.

9. The method according to claim 1, wherein the component (b) is one or more members selected from the group consisting of a polyvinyl butyral resin and a polyurethane resin.

10. The method according to claim 1, wherein the content ratio of the component (a) to the component (b), ((a)/(b)), is 2 or more and 40 or less.

11. The method according to claim 6, wherein the content ratio of (a) ethanol to the component (b), ((a)/(b)), is 2 or more and 40 or less.

12. The method according to claim 1, wherein the powder is one or more selected from the group consisting of a coloring pigment, a constitutive pigment, a pearl pigment, and an organic powder.

13. The method according to claim 1, wherein the content of the powder is 1 mass % or more and 99 mass % or less in the cosmetic used in (B).

14. The method according to claim 1, wherein the cosmetic used in (B) is a cosmetic selected from the group consisting of a makeup cosmetic and an UV protective cosmetic.

15. The method according to claim 12, wherein the mass ratio of the coloring pigment to the total powder in said powder-containing cosmetic is 0.2 or more.

16. The method according to claim 1, wherein the content of the component (a) is 55 mass % or more and 96 mass % or less in the composition, and the content of the component (b) is 4 mass % or more and 45 mass % or less in the composition.

17. The method according to claim 1, wherein the content of the component (a) is 60 mass % or more and 94 mass % or less in the composition, and the content of the component (b) is 6 mass % or more and 40 mass % or less in the composition.

18. The method according to claim 1, wherein the component (a) is a volatile substance comprising at least ethanol, and the component (b) is one or more selected from the group consisting of a polyvinyl butyral resin and a polyurethane resin.

19. The method according to claim 1, wherein said continuous fibers have a thickness of 10 nm to 3,000 nm.

20. The method according to claim 1, wherein said coating has a basis weight of 0.1 g/m$^2$ to 30 g/m$^2$.

21. The method according to claim 20, wherein said polymer is water-insoluble.

22. A method for producing a cosmetic coating on a skin surface, the method comprising
   (A) electrostatically spraying a composition comprising
   component (a) one or more volatile substances selected from the group consisting of water, an alcohol and a ketone, and component (b) a polymer having a film-forming ability directly onto the skin to form a coating comprising a deposit of continuous fibers on the skin surface; and
   (B) subsequently applying by a method other than electrostatic spraying a powder-containing cosmetic on the formed coating,
   wherein:
   said continuous fibers have a length which is at least 100 times greater than their thickness,
   said continuous fibers have a thickness of 10 nm to 3,000 nm, and
   the content of the component (a) is 30 mass % or more and 98 mass % or less in the composition, and the content of the component (b) is 2 mass % or more and 50 mass % or less in the composition wherein the content ratio of the component (a) to the component (b), ((a)/(b)), is 2 or more and 40 or less.

23. The method according to claim 22, wherein said coating has a basis weight of 0.1 g/m$^2$ to 30 g/m$^2$.

24. The method according to claim 22, wherein said polymer is water-insoluble.

* * * * *